(12) United States Patent
Neubert et al.

(10) Patent No.: US 9,402,669 B2
(45) Date of Patent: Aug. 2, 2016

(54) METHOD FOR PRODUCING A MEDICAL IMPLANT FROM A MAGNESIUM ALLOY

(75) Inventors: Volkmar Neubert, Clausthal-Zellerfeld (DE); Robert Schavan, Willich (DE)

(73) Assignee: Syntellix AG (DE)

( * ) Notice: Subject to any disclaimer, the term of this patent is extended or adjusted under 35 U.S.C. 154(b) by 327 days.

(21) Appl. No.: 14/343,161

(22) PCT Filed: Aug. 28, 2012

(86) PCT No.: PCT/EP2012/066683
§ 371 (c)(1),
(2), (4) Date: Apr. 2, 2014

(87) PCT Pub. No.: WO2013/034466
PCT Pub. Date: Mar. 14, 2013

(65) Prior Publication Data
US 2014/0236155 A1    Aug. 21, 2014

(30) Foreign Application Priority Data

Sep. 6, 2011 (DE) .......................... 10 2011 082 210

(51) Int. Cl.

| | |
|---|---|
| A61B 17/86 | (2006.01) |
| A61B 17/04 | (2006.01) |
| A61B 17/80 | (2006.01) |
| B22F 5/00 | (2006.01) |
| A61B 17/84 | (2006.01) |
| A61L 31/02 | (2006.01) |
| A61B 17/00 | (2006.01) |

(52) U.S. Cl.
CPC ........... *A61B 17/866* (2013.01); *A61B 17/0401* (2013.01); *A61B 17/80* (2013.01); *A61B 17/846* (2013.01); *A61L 31/022* (2013.01); *B22F 5/00* (2013.01); *A61B 2017/00004* (2013.01)

(58) Field of Classification Search
CPC .... A61B 17/866; A61B 17/846; A61B 17/80; A61B 17/0401; B22F 5/00
USPC .............................. 606/77, 300–331; 419/30
See application file for complete search history.

(56) References Cited

FOREIGN PATENT DOCUMENTS

DE           101 28 100 A1    12/2002

OTHER PUBLICATIONS

Heinz Haferkamp et al.; Alloy Development, Processing and Applications in Magnesium Lithium Alloys; The Japan Issue of Metals; Special Issue on Science and Technology for Advanced Magnesium Alloys; vol. 42, No. 7 (2001) pp. 1160-1166; XP-002686415.

(Continued)

*Primary Examiner* — Christopher Beccia
(74) *Attorney, Agent, or Firm* — Roger D. Emerson; Emerson Thomson Bennett, LLC

(57) ABSTRACT

A method for producing a medical implant, such as a bone screw, a bone nail, a bone pin, a plate, a suture anchor, etc. for fastening soft parts, such as tendons, muscles, and ligaments, to a bone, or in the form of an endoprosthesis or at least a part thereof, from a magnesium alloy having a magnesium fraction of at least 80 wt %, in particular of at least 90 wt %, including the following steps: a) melting the magnesium alloy to obtain an alloy melt, b) atomizing the alloy melt under a protective-gas atmosphere and cooling the atomized alloy melt to below the solidification point thereof in order to obtain an alloy powder, c) shaping the alloy powder by pressing to obtain an alloy green body, d) extruding the alloy green body to obtain a magnesium alloy molded part, and e) producing the medical implant from the magnesium alloy molded part.

9 Claims, 2 Drawing Sheets

(56) References Cited

OTHER PUBLICATIONS

Figure 1:
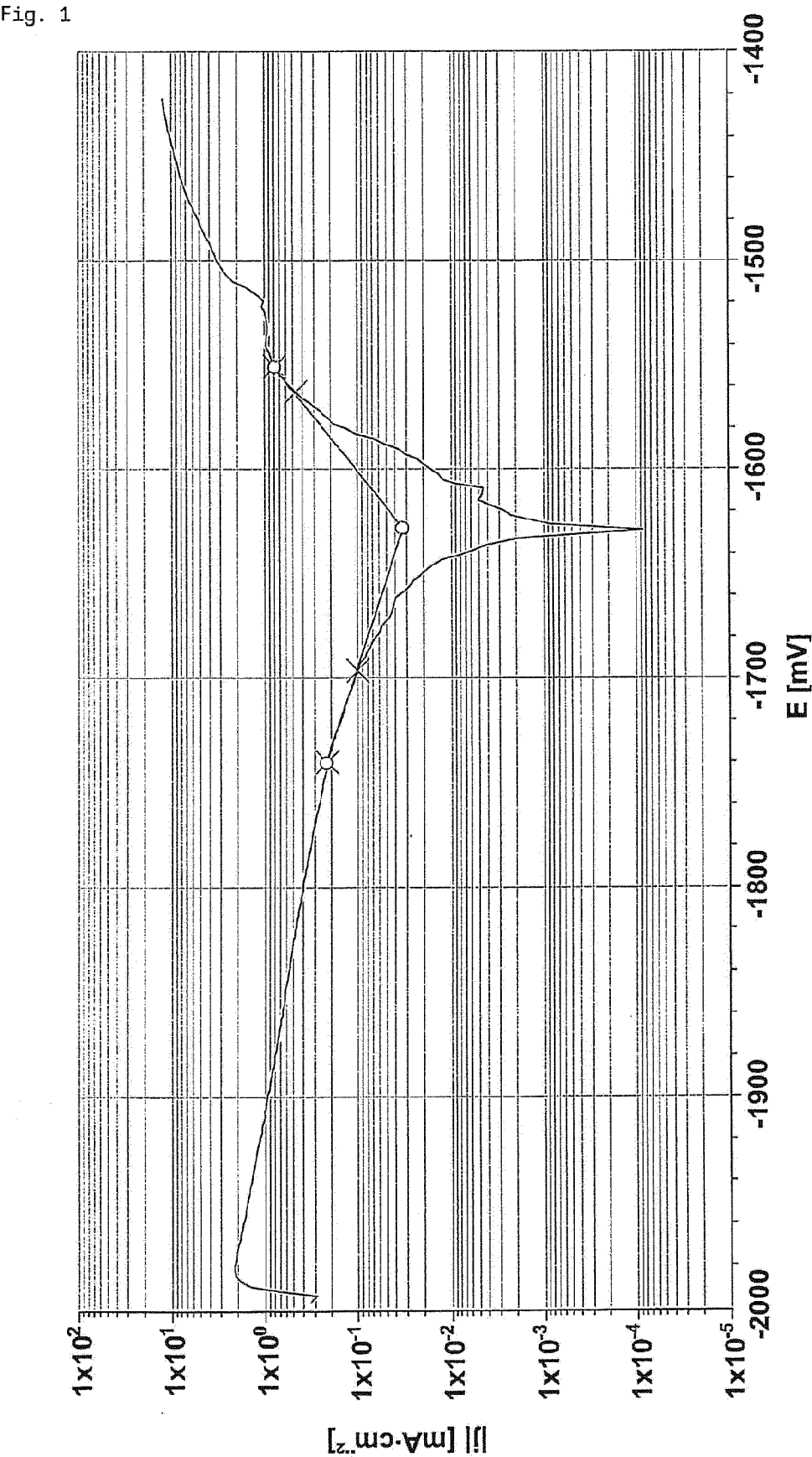

Bohumil Smola et al.; Microstructure, corrosion resistance and cytocompatibility of Mg-5Y-4Rare Earth-0.5Zr (WE54) alloy; Materials Science and Engineering C (2012); pp. 659-664; XP-002686416.

C. Labrecque et al.; Inverted Disk Centrifugal Atomization of AZ91 Magnesium Alloy; Canadian Metallurgical Quarterly; vol. 36, No. 3; pp. 169-175, 1997; XP-002686417.

International Search Report, as issued in corresponding International Patent Application No. PCT/EP2012/066683; 6 pages.

METHOD FOR PRODUCING A MEDICAL IMPLANT FROM A MAGNESIUM ALLOY

The present invention relates to a method for producing a medical implant, particularly in the form of a bone screw, a bone nail, a bone pin, a plate, a suture anchor, or the like for attaching soft tissues, especially tendons, muscles and ligaments, to a bone, or in the form of an endoprosthesis or at least a part thereof, made from a magnesium alloy having a magnesium content of at least 80% by weight. The invention is also directed to a moulded magnesium part that is obtainable by the aforementioned process.

In the medical field, permanent metal implants are available for splinting bone bridges and stabilising osteotomies, but they must be removed surgically after successful healing. Polyglycolide or polylactide implants also exist, and although these are bioresorbable and thus no longer need to be removed, in certain circumstances they are not able to satisfy all mechanical requirements.

A biocompatible component for clinical use, which is constructed from a binder and biocompatible metallic materials such as stainless steel, titanium, titanium alloys and chromium-cobalt based alloys, also ceramics and calcium phosphates, is known from DE 10 2008 008 219 A1. In order to prepare the biocompatible component, the biocompatible material is mixed with the binder and formed into the desired shape in an injection moulding process.

A bone screw that is intended in particular as an anchor screw for spongy bone tissue and can be made from bioresorbable material, is known for example from DE 20 2005 006 076 U1. However, the origin of the bioresorbable material is not disclosed in this case.

Besides the implant types described in the preceding, bioresorbable metal implants on the basis of magnesium alloys have recently come into use. Such implants are typically characterized by a high magnesium content in the alloy, typically above 80% by weight. Having been implanted surgically, such implants are slowly dissolved by the body's own decomposition mechanisms, some of the implant material being converted directly into bone material.

Such biodegradable magnesium alloys and the use thereof as medical implants are known from WO 2007/035791 A2 and WO 2007/125532 A1. In order to control their strength and rate of corrosion, the magnesium alloys contain a number of metal alloy additives such as neodymium, yttrium, zirconium, zinc, calcium, and other rare earth elements. The alloys described herein are moulded into the desired shape by means of casting or mechanical forming processes. However, it has been found that the mechanical strength and the resistance to corrosion of such implants often fail to reach the required performance levels. Consequently, in order to obtain sufficient strength and reduce the corrosion rate to an acceptable level, for example, it is necessary to use a number of alloy additives. These are expensive aggregates, and at least some of these cannot be broken down without difficulty in the human body.

Finally, from DE 101 28 100 A1 it is known to manufacture an implant from a magnesium alloy having general formula NgLi4Al4SE2 in smelting or powder-metallurgical processes, or by mechanical alloying, or to produce prefabricated implants by injection moulding or sintering techniques. In the formula cited in the preceding, SE stands for a rare earth metal. However, although the application cited includes a description of powder-metallurgical processing of magnesium alloys, it does not contain any information about how this is to be done in detail. Yet this is crucially important, especially when dealing with the highly pyrophoric magnesium alloys.

The object of the present invention is to provide a method with which a medical implant may be manufactured having improved mechanical strength and a reduced rate of corrosion under electrolytic conditions, such as prevail in human or animal bodies. A medical implant having the aforementioned properties is also to be provided.

This object is achieved with a method for producing a medical implant, particularly in the form of a bone screw, a bone nail, a bone pin, a plate, a suture anchor or the like for attaching soft tissues, particularly tendons, muscles and ligaments, to a bone, or in the form of an endoprosthesis or at least a part thereof, from a magnesium alloy having a magnesium content of at least 80% by weight, particularly at least 90% by weight, comprising the following steps:

a) melting the magnesium alloy to obtain an alloy melt,
b) atomising the molten alloy in a protective gas atmosphere and at the same time cooling the atomised molten alloy to below the solidification point thereof to obtain an alloy powder,
c) shaping the alloy powder by compaction to obtain an alloy green body,
d) extruding the alloy green body to obtain a magnesium alloy moulded article, and
e) producing the medical implant from the magnesium alloy moulded part.

Surprisingly, it has been found that with the method according to the invention it is possible to produce a magnesium alloy moulded article having improved mechanical strength compared with an alloy moulded part of the same composition prepared by conventional casting techniques. More surprisingly, a magnesium alloy moulded article manufactured with the method described is further characterized by reduced susceptibility to corrosion. In other words, the rate of dissolution thereof under electrolytic conditions such as prevail in a human or animal body, is slower than for a cast alloy moulded part having the same composition.

As a consequence of these property improvements, a medical implant made from a magnesium alloy moulded part according to the invention has greater mechanical strength, and this also be maintained over a longer period of time, and at the same time the implant is to a very large extent bioresorbable, rendering subsequent surgical removal unnecessary.

In a refinement of the method according to the invention, in step b) the alloy melt is at a temperature from 750 to 925° C., particularly from 775 to 850° C. during atomisation. This is particularly advantageous, because at these temperatures an alloy powder having a relatively narrow particle size distribution is obtainable.

Also in step b) in the method according to the invention, atomisation may take place under a pressure from 15 to 25 bar, particularly 17 to 23 bar. Moreover, the atomisation of the alloy melt under the above pressure and temperature conditions is characterized by good reproducibility of the atomisation processes, that is to say reproducible alloy powders having a high degree of uniformity in terms of average particle size and a narrow particle size distribution are obtained.

According to the invention, it is provided that the atomisation in step b) is carried out in an inert gas atmosphere. This is necessary to the extent that, especially under the temperature conditions described, magnesium alloys are highly pyrophoric, and would ignite spontaneously under the influence of oxygen. The shielding gases that are usable according to the invention are therefore selected from the eighth main group of the periodic system, that is to say the noble gases, wherein argon and/or helium are preferred due to their inertness and their relatively low cost.

The alloy powders obtained after the atomising step b) typically have an average particle size of 5 to 50 μm, particularly from 10 to 30 μm. It is especially preferred if the particles of the alloy powder are mainly globular in shape. This facilitates the compaction that is provided in step c) to produce the alloy green body.

In a further embodiment of the inventive method, the compaction in step c) is carried out at a pressure of at least 80 bar, in particular at least 100 or even 150 bar, wherein the compacting operation is preferably carried out in cold isostatic conditions. For this purpose, the alloy powder is either deposited and enclosed in a lightweight metal container, for example, or it undergoes cold isostatic pressing to produce an alloy green body. In the latter method, the alloy powder is introduced into a rubber mould and is subjected on all sides to uniform compression with a gas, for example an inert gas under pressure at the levels described previously. This pressure is then maintained for a period of at least 10, preferably at least 15 minutes, for example, during which the alloy green body is formed.

In step d) of the method according to the invention, it is provided to convert the alloy green body into the magnesium alloy moulded item by means of an extrusion process. This step may be conducted in a manner known per se, wherein the alloy green body is preferably heated to a temperature from 250 to 450° C., particularly from 300 to 400° C., prior to the pressing step.

The extrusion may be carried out using a punch on a die, which is preferably at a temperature from 150 to 400° C., in particular from 200 to 375° C. Since the magnesium alloy reacts so violently with atmospheric oxygen, it is also advisable to conduct this process step under protective gas conditions of the kind described previously, that is to say in an argon and/or helium atmosphere, for example.

As is usual with extrusion, the outer form of the material for extrusion is determined by the die. Thus, for example, a round bar may be created with a diameter of 5, 6 or 7 mm.

The extruded round rod is the semifinished product leading to the magnesium alloy moulded body, which can then undergo further processing to make a medical implant.

In theory, the magnesium alloys that are usable in the method according to the invention may contain any alloy additives. For producing medical implants, however, the alloy additives and their amounts should only be used in quantities that are acceptable with regard to health considerations. Thus for example, a preferred magnesium alloy consists of from 2.5 to 5% by weight rare earth metals (neodymium mischmetal), 1.5 to 5% by weight yttrium, 0.1 to 2.5% by weight zirconium, 0.01 to 0.8% by weight zinc, the balance being magnesium and unavoidable impurities as applicable. The magnesium alloy particularly preferably consists of 5 to 9% by weight rare earth metals (neodymium mischmetal) including yttrium, from 0.1 to 0.8% by weight zirconium, 0.01 to 0.25% by weight zinc, the balance being magnesium and unavoidable impurities as applicable. A magnesium alloy with the aforementioned alloy additions is particularly well suited for conversion into a magnesium alloy moulded part in the course of the method according to the invention. This is characterized by particularly good mechanical stability and a reduced corrosion rate.

With regard to the total content of possible impurities, these are preferably present in quantities not exceeding 1% by weight. In particular, the magnesium alloy according to the invention is substantially free from aluminium, that is to say the aluminium content is preferably less than 0.5% by weight, particularly less than 0.1% by weight.

More preferably, the magnesium alloy may be prepared before step a) of the process according to the invention by melting the alloy components at 700 to 900° C., followed by thorough mixing. The magnesium alloy prepared in this way may initially be poured into ingot moulds prior to the step a), particularly at a temperature of 700 to 900° C.

A further object of the present invention relates to a medical implant, particularly in the form of a bone screw, a bone nail, a bone pin, a plate, a suture anchor or the like, for attaching soft tissues, especially tendons, muscles and ligaments, to a bone, or in the form of an endoprosthesis or at least a part thereof, which is obtainable by the inventive method.

The medical implant according to the invention may further be provided with a surface coating, particularly a surface coating to control the rate of corrosion. A coating based on calcium phosphates, magnesium phosphates or (OH, F, Cl) phosphates of magnesium or calcium, as well as mixtures of said substances lends itself well to this purpose.

In the following the present invention will be discussed in greater detail with reference to an exemplary embodiment.

In order to produce a medical implant, first a magnesium alloy with the following additives is created:
Rare earth elements including yttrium: 8.15% by weight
Zirconium: 0.79% by weight,
Zinc: 0.192% by weight,
the alloy also contains the following detectable impurities:
silicon: 0.02% by weight,
copper: 0.01% by weight,
iron: 0.013% by weight,
aluminium: 0.036% by weight.
The remainder is magnesium.

To prepare the magnesium alloy described above, magnesium and the alloy elements in the above-mentioned quantities are melted in a radiation oven (Naber, Hereus, 20 kW) at 900° C. in an argon atmosphere and thoroughly homogenized at this temperature for about 15 min. After the mixing, the alloy is poured into moulds at 850° C. and cooled to room temperature.

To produce a magnesium alloy moulded article from the alloy produced in this way, the magnesium alloy is first remelted and then undergoes gas atomization at an atomization temperature of 875° C. in an argon protective gas atmosphere (PSI2, Phoenix Industries). For this purpose, the alloy melt is finely atomised in a high speed gas stream consisting of said protective gas at 21 bar and at the same time cooled to below its melting point. A fine-grained globular alloy powder is obtained which, according to analysis by scanning electron microscopy, has an average particle size of about 50 μm. The determination of the particle size distribution showed that 70% of the particles had a diameter in a range −30 μm to +20 μm relative to the average particle diameter described above.

In the next step of the process, an alloy green body was produced from the alloy powder by cold isostatic pressing. For this purpose, the alloy powder is transferred to a rubber mould and exposed to even pressure on all sides by the aforementioned protective gas at a pressure of about 150 bar. This pressure is maintained for a period of about 15 min and the finished alloy green body is then removed. The alloy green body has the following dimensions: Ø75 mm, height 300 mm. A press from Fielding was used for this process step.

For extrusion, the alloy green body is heated to about 300° C. in an electrically heated resistance furnace and in an extruder manufactured by Fielding & Platt is pressed by a punch through a die with a circular aperture of 6 mm that has been preheated to 200° C. In this way, the magnesium alloy moulded part is obtained in the form of a round rod with a diameter of 6 mm. The extrusion is carried out with the following parameters:

| | |
|---|---|
| Pressure | 700 t |
| Speed | 5.5. m/s |
| Pressing ratio | 1:150 |

The magnesium alloy moulded part produced in this way is subsequently made into a medical implant such as a bone implant by methods known per se, such as machining.

In order to compare the mechanical properties and corrosion behavior, a magnesium alloy moulded part of identical composition was also produced, wherein a round rod with 6 mm diameter was prepared in a casting process. In the following, the mechanical properties and the corrosion resistance of the two (chemically identical) materials are compared.

Mechanical Properties:

The tensile tests were conducted in accordance with DIN EN 10002, sample form taking into account DIN 50125, Form B, 4×20.

| | Invention | Comparison sample |
|---|---|---|
| Yield strength 0.2% | 260 MPa | 117.3 MPa |
| Tensile strength | 290 MPa | 175.3 MPa |
| Expansion | 13.6% | 4.32% |
| Constriction | 14.01% | 5.76% |

Corrosion Behavior:

To measure corrosion behavior, of cyclic voltammograms (current-potential curves) were recorded for a magnesium alloy moulded part according to the invention and a cast part of identical composition under the following conditions:

Working electrode: Magnesium alloy
Electrode size: 20×10×10 mm
Counter electrode: Platinum plate
Reference electrode: Calomel electrode (+242 mV vs. SHE)
Electrolyte: Ringer solution (manufactured by Braun)
Electrolyte temperature: 37° C.
Feed rate: 10 mV/min The Ringer's solution consists of distilled water and the following salts in the amounts indicated per liter solution:
8.60 g NaCl
0.30 KCl
0.33 $CaCl_2$ Due to its composition, the electrolyte simulates the corrosive environment in the human body. For this reason, the electrolyte temperature was also raised to the average temperature of the human body and was not measured at room temperature.

Figure 2:
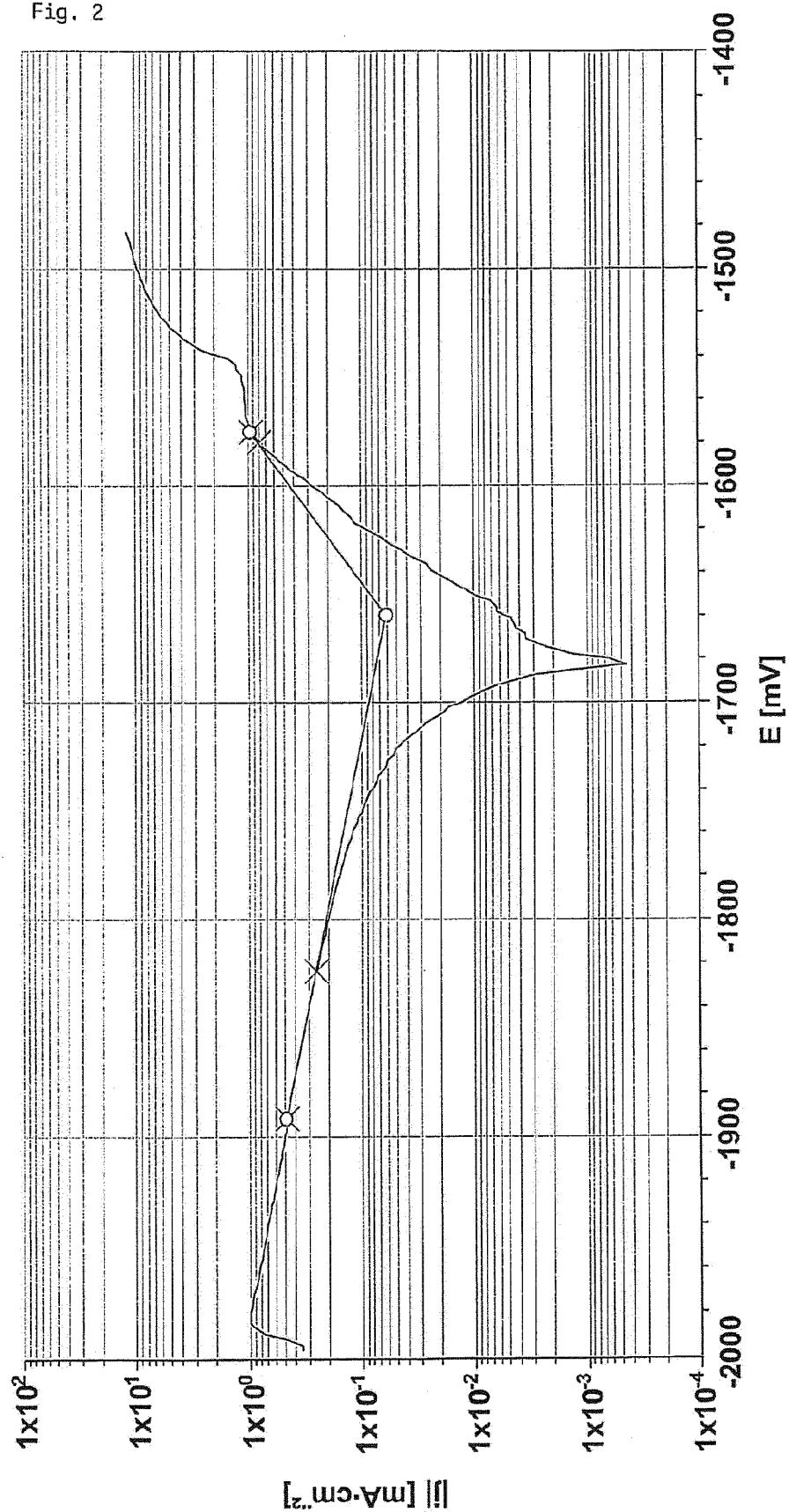

The results are shown as a graph plot dE/d log(i) in FIG. 1 (inventive magnesium alloy moulded part) and FIG. 2 (cast magnesium alloy moulded part comparison sample). From these plots, the following values for the corrosion potential and corrosion current density can be determined on the basis of the intersections of the plotted tangents of the cathodic and anodic branch:

| Sample | $E_{icorr}$ [mV] | $i_{corr}$ [µA/cm$^2$] |
|---|---|---|
| Invention (FIG. 1) | −1628 | 32.4 |
| Comparison (FIG. 2) | −1660 | 60.3 |

The corrosion current density $i_{corr}$ of the magnesium alloy moulded part according to the invention is only half as great, thereby confirming that the corrosion rate has been reduced significantly compared to the cast magnesium alloy moulded part with the same chemical composition. The magnesium alloy moulded part of the invention is consequently dissolved more slowly in the body and retains its support function for longer.

The invention claimed is:

1. A method for producing a medical implant, such as a bone screw, a bone nail, a bone pin, a plate, or a suture anchor for attaching soft tissues, such as tendons, muscles and ligaments, to a bone, or in the form of an endoprosthesis or at least a part thereof, from a magnesium alloy comprising a magnesium content of at least 80% by weight, a rare earth metal content from 2.5 to 5% by weight, an yttrium content from 1.5 to 5% by weight, a zirconium content from 0.1 to 2.5% by weight by weight, a zinc content from 0.01 to 0.8% by weight and unavoidable impurities, wherein the total content of possible impurities is less than 1% by weight and the aluminium content is smaller than 0.5% by weight, and the remainder contains magnesium up to 100% by weight, comprising the following steps:
a) melting the alloy components at 700 to 900° C. and then mixing them thoroughly to obtain a magnesium alloy, and pouring the magnesium alloy into moulds at a temperature of 700 to 900° C.,
b) melting the magnesium alloy to obtain an alloy melt,
c) atomising the alloy melt at a temperature from 775 to 850° C. and under a pressure from 17 to 23 bar in a protective gas atmosphere, and at the same time cooling the atomised alloy melt to below its solidification point to obtain an alloy powder,
d) shaping the alloy powder by compaction under cold istostatic conditions for obtain an alloy green body with at least 100 bar,
e) extruding the alloy green body to obtain a magnesium alloy moulded part, wherein the alloy green body is heated to a temperature from 300 to 400° C. before extrusion, and
f) producing the medical implant from the magnesium alloy moulded part.

2. The method according to claim 1, wherein in step c) the protective gas atmosphere is an inert gas atmosphere.

3. The method according to claim 1, wherein the alloy powder has an average particle size from 5 to 50 µm, and has a globular form.

4. The method according to claim 1, wherein the compaction in step d) is carried out at a pressure of at least 80 bar.

5. The method according to claim 1, wherein in step d) the pressure is exerted by means of a gas atmosphere.

6. The method according to claim 1, wherein step e) the extrusion is carried out using a punch on a die, which is at a temperature from 150 to 400° C.

7. The method according to claim 1, wherein the magnesium alloy comprises 5 to 9% by weight rare earth metals including yttrium, 0.1 to 0.8% by weight zirconium, 0.01 to 0.25% by weight zinc, the remainder being magnesium and unavoidable impurities.

8. A medical implant, such as a bone screw, a bone nail, a bone pin, a plate, or a suture anchor, for attaching soft tissues, such as tendons, muscles and ligaments, to a bone, or in the form of an endoprosthesis or at least a part thereof, produced by the method recited in claim 1.

9. The medical implant according to claim 8, wherein the implant is provided with a surface coating.

* * * * *